(12) United States Patent
Capella

(10) Patent No.: US 6,500,456 B1
(45) Date of Patent: Dec. 31, 2002

(54) COMPRESSED NITROGLYCERIN TABLET AND ITS METHOD OF MANUFACTURE

(75) Inventor: Roberto L. Capella, Landing, NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/508,705
(22) PCT Filed: Sep. 16, 1998
(86) PCT No.: PCT/US98/19356
§ 371 (c)(1), (2), (4) Date: May 22, 2000
(87) PCT Pub. No.: WO99/17766
PCT Pub. Date: Apr. 15, 1999

Related U.S. Application Data

(60) Provisional application No. 60/061,105, filed on Oct. 3, 1997.
(51) Int. Cl.[7] .............................. A61K 9/20; A61K 9/14
(52) U.S. Cl. ...................... 424/464; 424/465; 424/488; 424/484
(58) Field of Search ..................... 514/58, 778; 424/19, 424/464, 484, 35, 465, 488

(56) References Cited

U.S. PATENT DOCUMENTS 4,389,393 A * 6/1983 Schor et al. ................... 424/19
5,874,418 A * 2/2000 Stella et al. ................... 514/58

* cited by examiner

Primary Examiner—Thurman K. Page
Assistant Examiner—Blessing Fubara
(74) Attorney, Agent, or Firm—Charles Ashbrook

(57) ABSTRACT

The present invention is directed to a stable nitroglycerin containing pharmaceutical composition, preferably a tablet which is prepared by direct compression technology. The formulation closely replicates the properties of nitroglycerin molded sublingual tablets (e.g. adequate disintegration and sublingual absorption), while reducing the problems experienced with compressed tablets (e.g. friability and weight variations). The stable tablets are characterized by a decreased migration of nitroglycerin, decreased potency loss, excellent content uniformity when stored. The preferred combination of components are: nitroglycerin/lactose dilution, hydrous lactose, glyceril monostearate, fumed silica, pregelantinized starch and calcium stearate. The preferred process employs direct compression technology to yield composition showing adequate disintegration, bioavailability and improved stability.

19 Claims, No Drawings

COMPRESSED NITROGLYCERIN TABLET AND ITS METHOD OF MANUFACTURE

This Application is a 371 of PCT/US98/19356 filed Sep. 16, 1998 and also claims the benefit of Provisional No. 60/061,105 filed Oct. 3, 1997.

FIELD OF THE INVENTION

The present invention is directed to a nitroglycerin containing pharmaceutical composition, preferably a direct compressed tablet, stabilized by the presence of glyceryl monostearate. The formulation closely replicates the properties of nitroglycerin molded sublingual tablets (e.g., adequate disintegration and sublingual absorption), while reducing the problems experienced with compressed tablets (e.g., friability and weight variations). The stable tablets are characterized by a decreased migration of nitroglycerin, decreased potency loss, excellent content uniformity when stored. The preferred combination of components are: nitroglycerin/lactose dilution, hydrous lactose, glyceryl monostearate, fumed silica, pregelatinized starch and calcium stearate. The preferred process employs direct compression technology to yield a stabilized composition showing adequate disintegration and bioavailability.

BACKGROUND OF THE INVENTION

The stabilization of nitroglycerin in solid dosage forms has been a subject of scientific interest for more than twenty years. This interest can be attributed to the finding that nitroglycerin, which is a liquid at normal temperatures, easily migrates from tablets to other tablets and/or to the container and container components. Nitroglycerin will migrate to the cap-liner and to other tablets such as aspirin if the two products are stored together in the same container. Plastics have various affinities for nitroglycerin depending on their polarity; hence tablets have not been successfully marketed in unit dose containers. In fact, the USP states that nitroglycerin tablets must be stored in glass containers.

Various attempts have been made to improve the molded tablet formulation to assure better stability. However, as of now, significant improvements have not been made in marketed products. In 1973, Parke-Davis & Co. added polyethylene glycol 3350 to molded tablet formulations. While this additive reduced the migration and loss of nitroglycerin to some degree, the content uniformity range increased upon storage. Hence, after one or two years' shelf life, there was a risk of not meeting USP limits.

About this time, a number of stabilizing agents were screened and some were found to decrease the volatility of nitroglycerin in tablets. Among these were microcrystalline cellulose (MCC), polyvinylpyrrolidone (PVP), and β-cyclodextrin (BCD). For instance, a compressed tablet was prepared using the combination of MCC and PVP and marketed by Warner Chilcott Laboratories as NitroPRN®. The tablet was far superior to the current molded tablets with respect to nitroglycerin migration and volatility. However, the high amount of water insoluble excipient (MCC) was not desirable since the tablet gave a less acceptable feel and slower disintegration under the tongue.

Several patents on the stabilization of nitroglycerin in tablets have been granted. U.S. Pat. No. 4,091,091 assigned to Eli Lilly and Co., described the use of water soluble PVP to improve the stability of molded nitroglycerin tablets. In this application, PVP is added from a solution and molded tablets are made by the traditional method. Another patent, U.S. Pat. No. 4,059,686 assigned to Nippon Kayaku, indicates that β cyclodextrin is an effective stabilizing agent.

The manufacturing process for nitroglycerin sublingual tablets is typically the traditional molded tablet method. In this process, a wet mixture of nitroglycerin concentrate and other ingredients is made and, while moist, is pressed into cylindrical cavities. The wet tablets are pushed out using pins, which are accurately aligned to the cavities, and dried. The method produces a porous, fragile, rapidly dissolving tablet. However, a high degree of weight variation occurs and this attribute, coupled with inter-tablet migration of nitroglycerin, does not adequately preserve satisfactory content uniformity upon storage. The higher content variation which occurs after aging of the tablets, even when stored in tightly closed glass containers, is attributed to inter-tablet migration.

Moreover, this method has certain disadvantages; among them are the need to incorporate stabilizing agents like PVP, or the nitroglycerin itself, in alcohol and the subsequent removal of this solvent. It is preferable to employ nitroglycerin in a non-alcoholic solution for safety purposes. Also, wet granulations may require a binder which would retard and reduce the release (dissolution) of nitroglycerin from the tablet matrix. In addition, the extra handling and safety concerns with the processing of a wet granulation make the use of this technique less desirable.

The preferable method to prepare an improved stabilized nitroglycerin tablet appears to be the use of a direct compression technology. By this means the complexity and safety concerns with the wet granulation process is obviated. Although much is known about the problem of nitroglycerin instability, an improved dry compression formulation which closely matches the original sublingual tablet has not been produced. Such a tablet would preferably meet the USP requirements for nitroglycerin molded tablets, be comparable to the molded tablets in texture, size and weight, and effectively reduce the potency loss and inter-tablet migration of the drug.

The literature reports a number of stabilized compositions, but none have been prepared by direct compression technology to mimic the properties of a molded tablet. The technology and formulation techniques used to prepare an improved nitroglycerin tablet, particularly one made by compression, have not been developed. The lack of technical improvement relates to the complexity of the formulation with respect to selection of excipients and stabilizing agents which can be used to closely mimic the physical and chemical attributes of molded tablets and afford a significantly improved stability, and similar disintegration and bioavailability.

SUMMARY OF THE INVENTION

It is an object of the invention to provide new and useful compressed nitroglycerin sublingual tablets that are not susceptible to intertablet migration of nitroglycerin.

It is also an object of the invention to provide new and useful compressed nitroglycerin sublingual tablets that offer improved weight control (i.e., low weight variation).

It is yet another object of the invention to provide new and useful compressed nitroglycerin sublingual tablets that achieve the same pharmacological activity as molded sublingual tablets.

It is yet another object of the invention to provide new and useful compressed nitroglycerin sublingual tablets that provide a comparable mouthfeel to molded sublingual tablets.

It is yet another object of the invention to use a non-explosive nitroglycerin triturate to manufacture nitroglycerin sublingual tablets.

It is yet another object of the invention to provide a pharmaceutical composition with no overcharge of nitroglycerin to prolong the shelf life.

It is yet another object of the invention to provide new and useful compressed nitroglycerin sublingual tablets whose manufacture removes the complexity of wet granulation procedures and the safety concerns associated to solvent use.

It is yet another object of the invention to provide new and useful compressed nitroglycerin sublingual tablets that are characterized by decreased nitroglycerin volatility and superior stability profiles.

It is yet another object of the invention to provide new and useful compressed nitroglycerin sublingual tablets that exceeds current USP requirements for assay and content uniformity.

The invention achieves these objects by employing a nitroglycerin compressed tablet dosage form which is more stable, exhibits less tablet to tablet weight and content uniformity variation and is less prone to powdering (low friability) than compositions prepared by molding techniques. It has now been discovered that pharmaceutical compositions, such as tablets, containing nitroglycerin comprised of: nitroglycerin, glyceryl monostearate, calcium stearate, silica, starch and lactose are stabilized against the migration of the active agent from tablet to tablet when such tablets are in contact with each other. The compositions are of the same taste and similar mouth feel as molded compositions which have been available heretofore. In addition, the nitroglycerin containing tablets exceed the USP specifications and are bioequivalent to molded tablets.

It has further been discovered that such pharmaceutical compositions can be prepared by a direct compression method. The use of direct compression technology provides compositions which can be readily produced in an inexpensive, facile, efficient, hazard free and environmentally safe manner. In the preferred embodiment of the invention, nitroglycerin, glyceryl monostearate, hydrous lactose, calcium stearate, pregelatinized starch and hydrophobic fumed silica are blended and then compressed to form the sublingual tablet.

Other benefits and advantages of the present invention will become readily apparent to those skilled in the art from the following detailed description of the invention and the appended claims.

DETAILED DESCRIPTION OF THE INVENTION

As indicated above, the active agent of the present invention is nitroglycerin. The novel pharmaceutical compositions of this invention can contain from about 0.5 to about 2 weight % of nitroglycerin, said weight % based on the total composition weight. This permits a variety of dosage strengths to be manufactured.

Pure nitroglycerin has a vapor pressure of about 0.00026 mm at 20° C. and is a violent explosive which must be handled with great care. Commercially available nitroglycerin is, therefore, diluted to a concentration of 10 weight %, prior to the undertaking of pharmaceutical compounding and processing. This concentration of nitroglycerin was previously considered as flammable, but new Department of Transportation regulations have reclassified nitroglycerin concentrations above 2% as explosive. For safety reasons, nitroglycerin is diluted to a concentration below 2 weight %.

In practice, it is desirable to have a nitroglycerin dilution at a range that is suitable to produce various strength tablets that are currently prescribed. One common dilution of a given percentage of nitroglycerin is readily compounded with additional excipients to produce the various strength tablets. While the strengths can be readily compounded using a 10% dilution, because of current regulations, compounding is performed, and exemplified herein, using a lower 1.95% dilution.

In the preferred embodiment, the diluent is comprised of the main ingredient, lactose. Lactose influences, to a great extent, the flow behavior, compressibility and the taste of the compositions. It has been discovered that the presence of greater than about 90%, preferably about 95 to about 98%, weight % of lactose, said weight % based on the diluent weight, is surprisingly advantageous. In terms of weight % based on total tablet weight, preferably about 85 to about 95, optimally about 88 to about 93, weight % of lactose is present.

There are many lactoses known to those skilled in the art that are included in the scope of the present invention. As an example which is not meant to limit the scope of the invention, there are a number of well known commercially available lactoses in the market such as anhydrous lactose and hydrated lactose forms—monohydrates (TABLETTOSE sold by Meggle Co. of Germany), hydrous lactose fine, hydrous lactose fast flow and hydrous lactose G-200. Different grades of hydrous or anhydrous lactose may be used that enable the preparation of tablets with good compressibility, low friability and quick disintegration as well as affording protection from flammability.

In alternate embodiments of the present invention, additional excipients are included in the diluent along with the lactose. One of these additional excipients is an anti-sticking agent.

During the investigation of additional excipients which can be introduced into the compositions of the present invention, it has been discovered that the presence of about 0.1 to about 1, optimally about 0.1 to about 0.5, preferably about 0.3 to about 0.5, weight % of silica (a silica preferably falling within the class of finely divided silica), said weight % based on the total tablet weight, is surprisingly advantageous. Use of the silica in conjunction with other specified ingredients such as the lactose helps the flow of the powder blend and prevents sticking of tablets to punches. Despite the hydrophobic nature of some silicas, the optimized level employed in the formulation does not affect tablet performance.

There are a number of silicas known to those skilled in the art, and the present invention is meant to broadly encompass all of these silicas. The silicas can be precipitated (SYLOID® sold by Davison Division, W. R. Grace Company) or fumed, amorphous, colloidal or crystalline and in an anhydrous or hydrous form. Fumed silica or silicon dioxide ($SiO_2$) is a colorless, tasteless amorphous powder that is insoluble in water and acids. These colloidal silica particles are sintered together in chain-like formations that possess surface areas of 50 to 400 $M^2/g$, depending upon the grade.

Hydrophobic fumed silicas are well known commercially available materials, e.g. AER-O-SIL® R-972 sold by Degussa, Inc. of Teterboro, N.J., CAB-O-SIL® N70-TS sold by Cabot Corp. of Tuscola, Ill., TULLANOX® 500 sold by Tulco, Inc., (all of which are preferred for use herein), of the general class of amorphous precipitated silicas but of the pyrogenic (fumed) type which provide, according to Kirk-Othmer's Encyclopedia of Chemical Technology (Third Edition) Vol. 20 at pages 768 and 778–779, an ultimate particle size of 1–100 nm, and an aggregate particle size of 2–3 μm. Hydrophobic silicas are discussed in Kirk-Othmer's Encyclopedia of Chemical Technology (Third Edition) Vol. 7 at pages 440–441.

The compositions of the present invention also include the presence of starch. There are many different starches known to those of skill in the art and the present invention includes, but is not limited to those listed in Grant & Hackh's Chemical Dictionary, Fifth Edition. A preferred starch of the present invention is pregelatinized starch. The starch is present in an amount from about 5 to about 15 weight %, preferably about 5 to about 10 weight %, based on the total tablet weight.

An important ingredient which is included in the compositions of the present invention is a stabilizer. As indicated above, nitroglycerin is a volatile compound that exhibits poor physical stability when formulated without a stabilizer. The presence of the stabilizer decreases the potency loss of nitroglycerin in tablets, and thus its addition is important. The preferred stabilizer of the present invention is glyceryl monostearate.

During the investigation of stabilizers which can be introduced into the compositions of the present invention, it has been discovered that the presence of about 0.05 to about 10, preferably about 1 to about 5, optimally about 1.5 to about 4 weight % of glyceryl monostearate, said weight % of glyceryl monostearate based on the total tablet weight, is surprisingly advantageous. Use of the glyceryl monostearate in the amounts specified above, in conjunction with other specified ingredients, leads to a compressed sublingual tablet possessing superior stability.

Glyceryl monostearate is a waxy material that decreases the disintegration time of nitroglycerin tablets. To overcome this adverse effect, the use of a disintegrant is preferably employed in the present invention. It is widely known to those of skill in the pharmaceutical development area what constitutes a disintegrant and the amounts to be employed in pharmaceutical compositions. Non-limiting examples of common disintegrants include one or more water dispersible cellulose derivatives such as microcrystalline cellulose, sodium croscarmellose, starch, and starch derivatives such as sodium carboxymethylstarch.

Initially, the diluted nitroglycerin is blended with a preblend of the stabilizer (i.e., glyceryl monostearate) and diluent (i.e., lactose). Then the anti-sticking agent (i.e., silica), more diluent and the disintegrant are added to the blend.

The conventional procedure for making compacts requires the addition of a lubricant to the mixture before compression. Compression is accomplished by subjection of the dry blend under pressures by moveable punches operating in a die wherein the blend is confined. The lubricants are necessary to allow the ready ejection of the formed compact and to prevent the binding of the punches in the die. Lubrication is required only at the tablet-die interface to prevent sticking of the newly formed compact to the die walls. However, existing practical approaches to tablet lubrication require homogeneous distribution of lubricant within the entire tablet formulation.

Although there are various tableting lubricants which are commercially available, it has been determined that the use of a hydrophobic lubricant is preferred. Even more preferred is a lubricant which is the alkali metal salt of a fatty acid. In the most preferred embodiment of the present invention it has been determined that calcium stearate is the lubricant of choice in the present invention (calcium stearate is a well known commercially available material, e.g. calcium stearate NF powder sold by Mallinckrodt of St. Louis, Mo.). During the investigation of other excipients which can be introduced into the compositions of the present invention, it has been discovered that the presence of about 0.1 to about 1, optimally about 0.1 to about 0.5, preferably about 0.3 to about 0.5 weight % of calcium stearate, said weight % of calcium stearate based on the total tablet weight, is surprisingly advantageous. Use of the calcium stearate in the amounts specified above, in conjunction with the other specified ingredients, leads to a decrease in tablet weight variation.

Another aspect of this invention relates to the process for preparing the novel stabilized nitroglycerin tablets having the compositions described hereinbefore. The process by which the stabilized nitroglycerin tablets are prepared comprises the steps of: (a) commingling nitroglycerin with lactose to produce a nitroglycerin dilution (current regulations require that the content of the active agent be about 2 percent); (b) adding and mixing the nitroglycerin dilution with an excipient or combination of excipients selected from the group described hereinbefore to produce a blend; (c) compressing the blend under a force of about 200 to about 800 kg; and (d) thereafter, recovering the blend as a compressed product having a hardness of about 1–4 kp.

One embodiment of the present invention provides for the preparation of the formulation by milling glyceryl monostearate along with a small portion of hydrous lactose. Similarly, hydrophobic fumed silica is milled along with a small portion of hydrous lactose. Diluted nitroglycerin is blended with the milled glyceryl monostearate/hydrous lactose mixture in a blender for 5 minutes. Most preferably, an intensifier-bar is turned during mixing. The milled hydrophobic fumed silica/hydrous lactose mixture an a disintegrant, such as pregelatinized starch are added and blended for about 5 minutes. A lubricant, such as calcium stearate, is then added.

Blending for the purposes of discovering the present invention has been accomplished through the use of a V-blender. It should be understood, however, that there are different blending techniques known by those skill in the art that may be used with similar results. Variations of all blending times discussed herein of ±50% are permitted to obtain blend uniformity.

Once the ingredients are thoroughly blended, the composition is preferably subjected to compression since it is preferred that the compositions of the present invention be tablets. Therefore, conventional tableting equipment and standard tableting procedures are applied to the blended mixture to prepare compacted sublingual nitroglycerin tablets having improved stability. Compression is accomplished by subjecting the blended mix to high pressures by moveable punches operating in a die wherein the tablet mix is confined.

In preparing a tablet, the thoroughly blended mixture is directly compressed into tablets on a tablet machine. While any tablet machine known to those skilled in the art may be used to compress the blended mixture into tablet, in a preferred embodiment, tablets are compressed on any rotary press with weight control at a force of about 200 to about 800 kg at an average speed of about 75 RPM (65–85 RPM). Most preferably, an instrumented tablet press is employed for better control of tablet weights.

In one embodiment, the tablets are packaged and/or stored for a period of time. Tablets can be packaged in glass amber vials (25–100 tablets per vial).

Physical Characteristics of Compressed Sublingual Compositions

It is a desirable characteristic of the compacted pharmaceutical tablets of the present invention to be bioequivalent to molded nitroglycerin tablets. In this invention, the bioavailability of the active ingredient is not impeded by the processing or the excipients added to make a stable compressed nitroglycerin sublingual tablet. The present invention is surprisingly advantageous by including excipients which are necessary to impart physical characteristics essential for manufacture with existing compaction equipment, but without having adverse effects on the availability of nitroglycerin.

The initial disintegration time of the compositions of the present invention is about 25 seconds. Preferably, the disintegration of the compositions of the present invention is on the order of about 10 to about 40 seconds. Most preferably, the disintegration of the compositions of the present invention is on the order of about 20 to about 30 seconds.

A free flowing granulation is crucial in quickly and evenly filling the die cavity during compression in a high speed press. Uneven or poor flow of granulation results in erratic filling of the die cavity and consequently, weight variation. Small differences in weight are magnified as large relative standard deviations for a tablet with an average weight as low as 35 mg. Because diluted nitroglycerin is a non-flowable, wet appearing mixture, it is a major contributor to flow problems in a powder blend. Without the aid of the excipients, the impedance to flow of granulation is expected to be seen at the highest strength (0.6 mg) where the greatest amount of nitroglycerin is incorporated into the blend.

The compressed nitroglycerin compositions of the present invention show less weight variation than previously known molded nitroglycerin compositions. The weight variations of the compositions of the present invention are less than about 3% RSD. Preferably, the weight variations of the compositions of the present invention are on the order of 1–2% RSD. Most preferably, the weight variations of the compositions of the present invention are about 1% RSD.

The compressed nitroglycerin compositions of the present invention also show better content uniformity than previously known molded nitroglycerin compositions. The content uniformity variations of the compositions of the present invention are less than about 4% RSD. Preferably, the content variations of the compositions of the present invention are on the order of about 1% RSD to about 3% RSD. Most preferably, the content variations of the compositions of the present invention are on the order of about 2% RSD.

In addition, the compressed nitroglycerin compositions of the present invention show significantly less friability than previously known molded nitroglycerin compositions, thus indicating improved structural integrity against external mechanical forces, e.g. during packaging, shipping, handling. The friability of the compositions of the present invention is less than about 1%. Preferably, the friability of the compositions of the present invention is less than about 0.5%.

Further, the compressed nitroglycerin compositions of the present invention show consistent thickness and hardness when compressed into tablets. The thickness of tablets compressed from the compositions of the present invention is about 0.07 to about 0.10". The hardness of tablets compressed from the compositions of the present invention is greater than about 1 kp. Preferably, the hardness of tablets compressed from the compositions of the present invention is on the order of about 1–4 kp. The tablet hardness is sufficient to enable handling without risk of tablet breakage.

It will be apparent to those skilled in the art that the compressed sublingual tablets of the present invention may be multilayer tablets and have various shapes, colors, and sizes. Further, it will be apparent that these tablets once formed may be coded and/or coated by a variety of procedures well-known to those skilled in the art. Still further, the coated tablets may be subjected to a polishing procedure or other routine processes, which have been carried out on compressed tablets prior to this invention.

The term "tablet" as used herein includes tablets of any shape and includes caplets, which are tablets having a capsule shape. If desired, a pharmaceutically acceptable coloring agent may be added to the tablets. The compressed tablets may also be coated with a pharmaceutically acceptable polymer, gelatin, or sugar coating. The addition of coloring agent, polymer, gelatin, or sugar coating can be accomplished by anyone skilled in the art.

While various listed ingredients in the specification and claims have the suffix "USP" (United States Pharmacopia) or "NF" (National Formulary), this is intended only to better identify the ingredient, or its purity, and not to limit the invention in any way to the use of ingredients so marked, since identical materials are available under other designations e.g. in foreign countries.

The present invention also comprises a product prepared by the methods of manufacturing the compressed nitroglycerin-containing compositions described above. The product is preferably a compressed nitroglycerin sublingual tablet prepared according to a process having the steps comprising: (a) blending ingredients selected from the group consisting of nitroglycerin, hydrous lactose, glyceryl monostearate, calcium stearate, starch and hydrophobic fumed silica; (b) compressing said blend under a pressure of 200 to about 800 kg; and (c) recovering said blend as a compressed product. In one embodiment, the process further comprises the step of diluting the nitroglycerin prior to blending the ingredients.

The preferred ingredients in the process are nitroglycerin, lactose monohydrate, calcium stearate, silica, starch and glyceryl monostearate in the following amounts: 0.5 to about 5 weight % of nitroglycerin; 88 to about 93 weight % of lactose; 0.3 to about 0.5 weight % of silica; 0.3 to about 0.5 weight % of calcium stearate; 5 to about 15 weight % of starch and about 0.5 to about 10 weight % of glyceryl monostearate. The products, preferably compressed into tablets, and made by the process have the following physical properties: disintegration on the order of about 20 to about 30 seconds; weight variations on the order of about 1 to about 2% RSD; content variations on the order of less than about 4% RSD; friability on the order of less than about 1%; thickness on the order of about 0.07"–0.10", and hardness on the order of about 1–4 kp.

The following non-limiting examples illustrate the best mode contemplated by the inventors of carrying out the present invention.

EXAMPLES

I. Summary

Two active lots (0.3 and 0.6 mg) were manufactured and the manufacturing process (milling, blending and compression) was successfully designed and the tablets satisfactorily met the physical and chemical stability requirements for a period of twelve months.

II. Process Description

A. Materials/Formulations

The examples presented below illustrate particular embodiments of the invention, and are not intended to limit the scope of the specifications or the claim in any way.

| Material | Example 1 | Example 2 |
| --- | --- | --- |
| Nitroglycerin 1.95% Mixture | 15.385 | 30.769 |
| Glyceryl Monostearate | 0.615 | 1.231 |
| Lactose Monohydrate | 16.730 | 3.880 |
| Silicon Dioxide | 0.065 | N/A |
| Pregelatinized | 2.100 | 4.000 |
| Calcium Stearate | 0.105 | 0.120 |

Note: No excess Nitroglycerin was used.

B. Equipment and Manufacturing Process (Active Batches)

The amount of Nitroglycerin USP weighed was calculated based on assay results. The total amount of Lactose Monohydrate needed was adjusted based on the amount of Nitroglycerin used.

Glyceryl Monostearate, NF (Myvaplex 600P) and Lactose Monohydrate, NF were milled together and collected in a drum. Silicon Dioxide and Lactose Monohydrate were milled together and collected in another drum. Diluted Nitroglycerin USP and the milled Glyceryl Monostearate/Lactose Monohydrate mix were loaded into a blender equipped with an intensifier bar. The ingredients were blended for ten minutes with the intensifier bar ON. Then, the milled Silicon Dioxide/Lactose Monohydrate mix and the Pregelatinized Starch were added to the PK blender and blended for five minutes with the intensifier bar ON. Calcium Stearate was added to the blender and the materials were blended for five minutes. The powder blends were compressed into tablets using suitable tablet press machine.

In these formulations, lactose was used as the diluent, pregelatinized starch as the disintegrant, glyceryl monostearate as the stabilizer, silicon dioxide as the flow-aid agent and calcium stearate as the lubricant.

C. Stability Results

Physical Stability

The following table shows the 12-month physical stability results (hardness and disintegration time) for Examples 1 and 2 stored in bottles of 25's and 100's at 25° C./60%RH and 40° C./75 %RH conditions. All results met the tentative hardness guidelines used during in-process testing and met the disintegration acceptance criteria of $\leq 2$ minutes. However, a small increase in tablet hardness and disintegration times was observed during storage.

|  |  | Example 1 | | Example 2 | |
|---|---|---|---|---|---|
| Stability Cond. | Time (Mo.) | 25's | 100's | 25's | 100's |
| Hardness (kp) | | | | | |
| Initial | 0 | 2.3 | | 1.6 | |
| 40° C./75% RH | 1 | 2.1 | 1.9 | 1.5 | 1.5 |
|  | 2 | 2.0 | 2.3 | 1.4 | 1.4 |
|  | 3 | 2.0 | 2.3 | 1.5 | 1.4 |
|  | 6 | 1.9 | 1.7 | 1.4 | 1.3 |
| 25° C./60% RH | 3 | 2.0 | 2.3 | 1.4 | 1.5 |
|  | 6 | 1.9 | 1.8 | 1.4 | 1.6 |
|  | 9 | 2.7 | 2.7 | 1.5 | 1.8 |
|  | 12 | 2.5 | 2.5 | 1.6 | 1.7 |
| Disintegration Time (seconds) | | | | | |
| Initial | 0 | 21 | | 27 | |
| 40° C./75% RH | 1 | 33 | 29 | 27 | 25 |
|  | 2 | 35 | 29 | 24 | 23 |
|  | 3 | 31 | 31 | 20 | 19 |
|  | 6 | 27 | 21 | 17 | 14 |
| 25° C./60% RH | 3 | 33 | 33 | 30 | 28 |
|  | 6 | 33 | 32 | 26 | 27 |
|  | 9 | 30 | 35 | 29 | 24 |
|  | 12 | 35 | 29 | 24 | 24 |

Content Uniformity

Tablet samples were tested for nitroglycerin content uniformity (CU) initially and after twelve months of storage at 25° C./60% RH. The results show low variability (RSD<2%) and the USP specification of 75.0–135.0% of Label Claim was met.

|  | Example 1 | | | Example 2 | | |
|---|---|---|---|---|---|---|
|  | Initial | 12 Months | | Initial | 12 Months | |
| Tablet No. | (Bulk) | 25's | 100's | (Bulk) | 25's | 100's |
| 1 | 100.3 | 99.0 | 98.7 | 104.3 | 100.5 | 98.6 |
| 2 | 100.3 | 98.4 | 97.1 | 101.6 | 99.6 | 99.7 |
| 3 | 97.8 | 99.9 | 97.8 | 101.5 | 102.6 | 100.5 |
| 4 | 101.6 | 98.9 | 99.3 | 104.2 | 100.5 | 98.9 |
| 5 | 99.8 | 100.7 | 99.6 | 100.9 | 100.7 | 100.6 |
| 6 | 100.3 | 99.7 | 100.7 | 103.2 | 99.3 | 105.1 |
| 7 | 101.0 | 100.6 | 98.5 | 102.4 | 100.3 | 100.5 |
| 8 | 96.3 | 100.0 | 97.4 | 100.6 | 100.2 | 99.8 |
| 9 | 97.4 | 97.9 | 96.1 | 103.3 | 102.0 | 98.9 |
| 10 | 99.1 | 97.8 | 97.5 | 101.5 | 100.7 | 98.9 |
| Average: | 99.4 | 99.3 | 98.3 | 102.4 | 100.6 | 100.2 |
| % RSD: | 1.7 | 1.1 | 1.4 | 1.3 | 1.0 | 1.9 |

Assay and Degradation Products

The following table shows the 12-month chemical stability results (assay and degradation products) for the two examples stored in bottles of 25's and 100's at 25° C./60% RH and 40° C./75 %RH conditions. All results met the USP assay specification of 90.0–115.0% LC and no significant change in degradation products was observed.

|  |  |  | Degradation Products | | | | |
|---|---|---|---|---|---|---|---|
|  |  |  | Weight % | | Area % | | |
| Stability | Time (Mo.) | Assay % LC | 1.3 DNG | 1.2 DNG | 2-MNG | 1-MNG | Clonitrate |
| Example 1 (25's) | | | | | | | |
| Initial | 0 | 100.9 | 0.4 | 0.2 | ND | ND | ND |
| 40° C./75% | 1 | 97.1 | 0.4 | 0.2 | ND | ND | ND |
|  | 2 | 99.0 | 0.4 | 0.2 | ND | ND | ND |
|  | 3 | 98.6 | 0.4 | 0.2 | ND | ND | ND |
|  | 6 | 97.2 | 0.4 | 0.2 | ND | ND | ND |
| 25° C./60% | 3 | 100.0 | 0.4 | 0.2 | ND | ND | ND |
|  | 6 | 99.6 | 0.4 | 0.2 | ND | ND | ND |
|  | 9 | 101.1 | 0.4 | 0.2 | ND | ND | ND |
|  | 12 | 100.4 | 0.4 | 0.2 | ND | ND | ND |

-continued

| Stability | Time (Mo.) | Assay % LC | Degradation Products | | | | |
|---|---|---|---|---|---|---|---|
| | | | Weight % | | Area % | | |
| | | | 1.3 DNG | 1.2 DNG | 2-MNG | 1-MNG | Clonitrate |
| Example 1 (100's) | | | | | | | |
| 40° C./75% | 1 | 98.4 | 0.3 | 0.2 | ND | ND | ND |
| | 2 | 96.5 | 0.3 | 0.2 | ND | ND | ND |
| | 3 | 95.8 | 0.3 | 0.1 | ND | ND | ND |
| | 6 | 95.6 | 0.3 | 0.1 | ND | ND | ND |
| 25° C./60% | 3 | 99.3 | 0.3 | 0.1 | ND | ND | ND |
| | 6 | 99.6 | 0.3 | 0.1 | ND | ND | ND |
| | 9 | 99.4 | 0.3 | 0.1 | ND | ND | ND |
| | 12 | 99.5 | 0.3 | 0.1 | ND | ND | ND |
| Example 2 (25's) | | | | | | | |
| Initial | 0 | 102.4 | 0.4 | 0.2 | ND | ND | ND |
| 40° C./75% | 1 | 100.6 | 0.4 | 0.2 | ND | ND | ND |
| | 2 | 99.9 | 0.4 | 0.2 | ND | ND | ND |
| | 3 | 100.7 | 0.4 | 0.2 | ND | ND | ND |
| | 6 | 98.4 | 0.4 | 0.2 | ND | ND | ND |
| 25° C./60% | 3 | 101.2 | 0.4 | 0.2 | ND | ND | ND |
| | 6 | 101.8 | 0.4 | 0.2 | ND | ND | ND |
| | 9 | 103.3 | 0.4 | 0.2 | ND | ND | ND |
| | 12 | 102.4 | 0.4 | 0.2 | ND | ND | ND |
| Example 2 (100's) | | | | | | | |
| 40° C./75% | 1 | 100.7 | 0.4 | 0.1 | ND | ND | ND |
| | 2 | 99.6 | 0.3 | 0.2 | ND | ND | ND |
| | 3 | 98.7 | 0.3 | 0.1 | ND | ND | ND |
| | 6 | 98.2 | 0.3 | 0.1 | ND | ND | ND |
| 25° C./60% | 3 | 100.8 | 0.3 | 0.1 | ND | ND | ND |
| | 6 | 101.1 | 0.3 | 0.1 | ND | ND | ND |
| | 9 | 103.1 | 0.4 | 0.2 | ND | ND | ND |
| | 12 | 102.5 | 0.3 | 0.2 | ND | ND | ND |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A stable composition comprising effective amounts of nitroglycerin, lactose, silica, starch, a stabilizer comprising glyceryl monostearate in an amount of about 0.5 to 10 weight %, and a lubricant, wherein nitroglycerin is the sole pharmacologically active agent.

2. The composition of claim 1 wherein the composition is available as a sublingual tablet.

3. The composition of claim 1 wherein the starch is pregelatinized starch used a disintegrant.

4. The composition of claim 1 wherein the silica is a fumed silica.

5. The composition of claim 1 wherein the lubricant is an alkali metal salt.

6. The composition of claim 1 wherein the lactose is hydrous lactose.

7. The composition of claim 1 comprising the following amounts: 0.5 to about 5 weight % of nitroglycerin; greater than about 90 diluent weight % of lactose; 0.1 to about 1 weight % of silica; 0.1 to about 1 weight % of calcium stearate; 5 to about 15 weight % of starch and about 0.5 to about 10 weight % of glyceryl monostearate.

8. The composition of claim 1 wherein the composition disintegrates on the order from about 20 to about 30 seconds.

9. The composition of claim 1 wherein the variation in weight of the composition is about 1 to about 2% relative standard deviation (RSD).

10. The composition of claim 1 wherein the composition has the following properties: disintegration on the order of about 20 to about 30 seconds; weight variations on the order of about 1 to about 2% relative standard deviation (RSD); content variations on the order of less than about 4% relative standard deviation (RSD); friability on the order of less than about 1%; thickness on the order of about 0.07–0.10", and hardness on the order of about 1–4 kp.

11. The composition of claim 1 wherein the composition is a compressed tablet.

12. A stable compressed tablet consisting essentially of effective amounts of nitroglycerin, lactose, silica, pregelatinized starch, glyceryl monostearate, and lubricant, wherein nitroglycerin is the sole pharmacologically active agent.

13. The composition of claim 12 wherein the silica is fumed silica.

14. The composition of claim 13 wherein the lubricant is calcium stearate.

15. The composition of claim 14 wherein the lactose is hydrous lactose.

16. A dry, compressed product containing nitroglycerin produced by the steps comprising: (a) commingling nitroglycerin with lactose to produce a nitroglycerin dilution in which the content of the active agent is about 2 percent or less; (b) adding and mixing the nitroglycerin dilution with silica, lubricant, glyceryl monostearate, starch, and optionally additional lactose to produce a blend; (c) compressing the blend; and (d) thereafter, recovering the blend as a compressed product.

17. The product of claim 16 wherein the starch is pregelatinized starch.

18. A process for preparing a dry, compressed product containing nitroglycerin produced by the steps comprising:

(a) commingling nitroglycerin with lactose to produce a nitroglycerin dilution in which the content of the active agent is about 2 percent or less; (b) adding and mixing the nitroglycerin dilution with silica, lubricant, glyceryl monostearate, starch, and optionally additional lactose to produce a blend; (c) compressing the blend; and (d) thereafter, recovering the blend as a compressed product.

19. A stable composition comprising effective amounts of nitroglycerin, lactose, silica, starch, a stabilizer consisting essentially of glyceryl monostearate in an amount of about 0.5 to 10 weight %, and a lubricant, wherein nitroglycerin is the sole pharmacologically active agent.

* * * * *